United States Patent [19]
Campbell

[11] Patent Number: 5,640,149
[45] Date of Patent: Jun. 17, 1997

[54] VENTILATOR DISCONNECT ALARM

[75] Inventor: Duncan Campbell, Glebe, Australia

[73] Assignee: Ulco Engineering Pty. Ltd., Merrickville, Australia

[21] Appl. No.: 301,861

[22] Filed: Aug. 31, 1994

[30]  Foreign Application Priority Data

Aug. 31, 1993 [AU] Australia ................. PM0926

[51] Int. Cl.$^6$ .................................. G08B 21/00
[52] U.S. Cl. ................ 340/626; 340/606; 340/611; 128/204.21
[58] Field of Search ................. 340/626, 606, 340/611; 128/204.21, 204.22, 204.23, 202.22

[56]  References Cited

U.S. PATENT DOCUMENTS

| | | | |
|---|---|---|---|
| 3,741,208 | 6/1973 | Jonsson et al. | 128/145.6 |
| 4,155,357 | 5/1979 | Dahl | 128/145.8 |
| 4,393,869 | 7/1983 | Boyarsky et al. | 128/204.18 |
| 4,766,894 | 8/1988 | Legrand et al. | 128/204.21 |
| 4,915,103 | 4/1990 | Visveshwara et al. | 128/204.23 |
| 5,161,525 | 11/1992 | Kimm et al. | 128/204.21 |
| 5,178,151 | 1/1993 | Sackner | 128/672 |
| 5,373,842 | 12/1994 | Olsson et al. | 128/204.21 |
| 5,400,778 | 3/1995 | Jonson et al. | 128/204.23 |

FOREIGN PATENT DOCUMENTS

| | | | |
|---|---|---|---|
| 99743 | 2/1984 | European Pat. Off. | A61M 16/00 |
| 257355 | 3/1988 | European Pat. Off. | A61M 16/00 |
| 1460816 | 1/1977 | United Kingdom | A61M 16/00 |

*Primary Examiner*—Jeffery Hofsass
*Assistant Examiner*—Ashok Mannara
*Attorney, Agent, or Firm*—David P. Gordon

[57]  ABSTRACT

On method of sensing a ventilation failure measures a ventilation cycle and if the pressure is not maintained throughout the whole of an inspiration period above the setting for the low datum point 10 an alarm is signaled. A normal ventilation cycle is shown in FIG. 1(a) with the pressure over the ventilation cycle indicated by curve 14, low pressure datum 10 and the high pressure datum 12. The inspiration period 16 occurs for a given length of the cycle 14. When the tube feeding air to the patient is disconnected (whether wholly or partially) the ventilation cycle is as shown in FIG. 1(b). Inspiration peak 18 is now much lower and pressure drops rapidly, once the given volume has been delivered, from peak 18 to below set low pressure datum 10 (before termination of period 16). The peak 18 and the slope of the curve as indicated at 20 will vary depending upon the circumstances experienced. Another method measures the period between excursions of the pressure above a given level above datum 10.

6 Claims, 4 Drawing Sheets

VENTILATOR DISCONNECT ALARM

FIELD OF THE INVENTION

This invention relates to an apparatus and a method to indicate when a ventilating apparatus has been disconnected from a patient or there is a failure to adequately ventilate a patient.

BACKGROUND OF THE INVENTION

When ventilation of an anaesthetised patient is required during surgery a tube is attached from a mechanical ventilator to the patient's mouth or trachea. Ventilators performing this function are typically equipped with a number of safety features to check whether the patient is properly ventilated. One form of testing relies on measuring the pressure of the gas supplied to the patient.

Dysfunction of the ventilator includes sensing when too high a supply pressure is delivered, too low a supply pressure is available, or there is an absence of the expected cyclic pressure pattern of a typical ventilation cycle. The cyclic pattern is determined by measuring whether the pressure excursions traverse a set level within a given (inspiration) period. Once an unsafe condition has been detected an alarm of some type is activated. A delay is generally employed to obviate a false alarm. In the sensing of the absence of the cyclic pattern a delay of from fifteen to twenty five seconds may be employed while in the case of the sensing of a high or low pressure a delay of typically one second is employed before the alarm is activated.

Due to the variability in the circumstances during surgery and considering individual differences between patients the fixing of the pressures at which the alarms will activate in either the low or high pressure conditions is set by the attending physician upon observing the pressure variation of the patient during a ventilation cycle.

Notwithstanding these features a loss of intubation of the patient may not be detected until after the appropriate delay has passed or may not be detected at all if the window defining the limits of upper and lower pressure specified by the attending physician is inappropriately adjusted. The disconnected line may still show the required cycling within the stipulated bounds and no alarm would be indicated.

A further safety feature during anaesthesia is the provision of capnography, measuring the amount of carbon dioxide in the exhaled breath of the patient. In the absence of sufficient carbon dioxide being measured an alarm is sounded after a delay of fifteen to twenty seconds. Other monitors are also used to check for the signs of proper ventilation of a patient, for example a pulse oximeter measures the oxygen in the blood of a patient's finger employing an optical technique but involves an even longer delay before sounding an alarm.

SUMMARY OF THE INVENTION

The present invention seeks to overcome these disadvantages in the prior art or at least to provide an alternative which provides a more responsive indication of a failure to adequately ventilate a patient.

According to a first aspect of the invention there is provided a method for supervising the operation of a ventilating apparatus and for indicating a failure to adequately ventilate an intubated patient including measuring the pressure supplied to a patient over a ventilation cycle with an alarm being activated if the pressure is not maintained throughout the whole of an inspiration period above a set low datum point.

According to a further aspect of the invention there is provided a method for supervising the operation of a ventilating apparatus and for indicating a failure to adequately ventilate an intubated patient including determining the inspiration period of an intubated patient, indicating when the duration of a subsequent inspiration period of a ventilation cycle differs from said period and signalling an abnormal condition under such indication.

According to yet a further aspect of the invention there is provided an apparatus for indicating an abnormal ventilation of a patient including means to sense the pressure supplied to a patient during a cycle of a ventilator, means to determine the duration of a ventilation cycle of a ventilator and means sensitive to the duration of a ventilation cycle and said pressure supplied to a patient to indicate an abnormal operation of the ventilator when the ventilation period is less than a predetermined duration or the pressure is not maintained throughout the whole of an inspiration period above a set low datum point.

BRIEF DESCRIPTION OF THE DRAWINGS

Embodiments of the invention will now be described with respect to the following drawings, in which.

DETAILED DESCRIPTION OF THE PREFERRED EMBODIMENTS

The description of this embodiment has reference to a ventilator of the type having a timed-cycle, and being volume limited such as described in GB 1,488,317.

Figure 1:
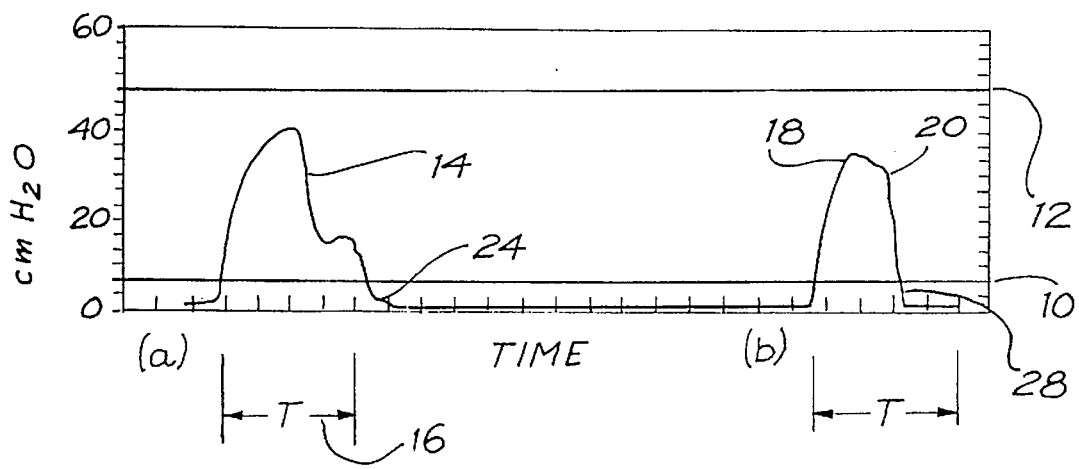
FIG. 1 shows graphically how the present invention works.

Referring to FIG. 1 (a), a typical ventilation cycle is shown. The low pressure datum is shown at 10 while the high pressure datum is shown at 12 and the pressure over the ventilation cycle is indicated by curve 14. The inspiration period 16 occurs for a given length of the cycle 14. When the tube feeding air to the patient is disconnected (whether wholly or partly) the ventilation cycle is as shown in FIG. 1 (b).

The inspiration peak 18 is now much lower and the pressure drops rapidly once the given volume has been delivered from the peak 18 to below the set low pressure level 10 before termination of period 16. The peak 18 and the slope of the curve as indicated at 20 will vary depending upon the circumstances experienced. In principle, with a whole or partial disconnect the absence of the full (capacitive) load presented by the patient's lungs means that the ventilator is presented with a load of high (possibly infinite) compliance into which the fixed volume source can feed.

One method of sensing that a ventilation cycle is of the form shown in FIG. 1 (b) is if the pressure is not maintained throughout the whole of an inspiration period above the setting for the low datum point 10.

Another method would be to measure the period between excursions of the pressure above a given level (other than the low datum point 10) but less than the peak 18 provided sufficient resolution between the normal and the abnormal states was available to give reliable indications.

A single cycle is all that is required for the abnormal condition to be indicated allowing the problem to be attended to rapidly. Neither variations in the window, that is the bounds for the upper and lower pressure limits or datum points 10, 12, nor changes in the flow of gas to the patient can interfere with the operation of this type of alarm.

Figure 2:
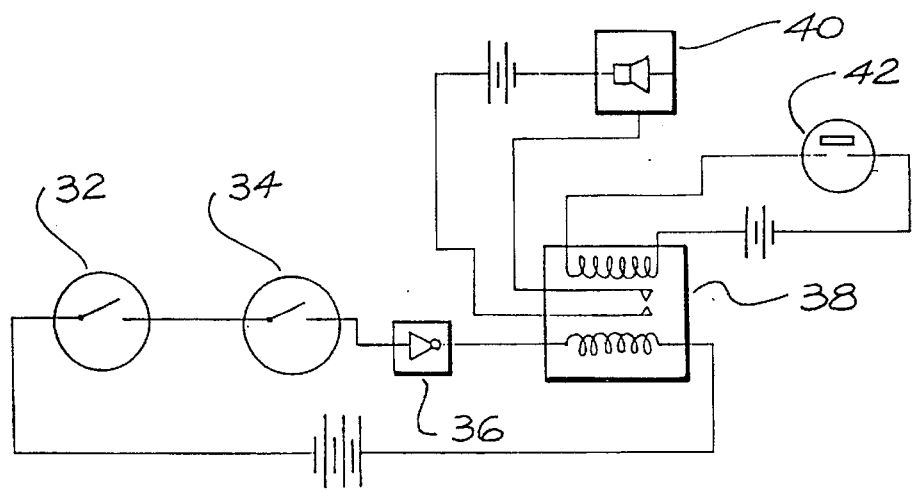
FIG. 2 shows a block diagram of a circuit implementing a first embodiment of the invention.

A simple circuit for implementing the alarm according to the invention is shown in FIG. 2.

Two pressure switches 32 and 34 and a delay 36 are connected in series to a triggering circuit 38. Triggering circuit 38 activates an alarm 40. Alarm 40 may be a flashing light, an audible alarm or a combination of these. For example, a flashing light may operate for 10 seconds before sounding an audible alarm. Triggering circuit 38 would, for example, be a bistable element well known in the art and suitable for use in an anaesthetic environment (where explosive or inflammable gases are common). Triggering 38 may be reset manually by push button 42.

In this embodiment pressure switch 32 is closed during each inspiration phase of the ventilator. Pressure switch 34 closes when the circuit pressure drops below, for example 7 cm. $H_2O$. During normal operation with reference to FIG. 1 (a) pressure switch 32 will be closed throughout the full period 16 with pressure switch 34 only closing during interval 24 of the cycle 14 corresponding to the pressure being below the datum 10, and will be open during the remainder of the pressure cycle 14. Hence the alarm will not be triggered.

Under the abnormal conditions indicated in FIG. 1 (b) pressure switch 32 will be shut for the full inspiration period 16 during which time switch 34 will 20 be closed in the interval 28. Hence both switches 32 and 34 will be shut during interval 28 triggering the alarm 40 via circuit 38.

Pressure switches 32 and 34 are adjusted such that during each ventilation cycle switch 32 closes after switch 34 has opened. The delay 36 allows a sufficient time interval for switch 34 to fully open before switch 32 closes. A delay of 0.1 second should be sufficient for the delay 36.

The invention has particular application to ventilators using time or volume cycling as their cycling is unaffected by a circuit disconnection and the absence of any rate change may fail to attract attention. The invention can be used with ventilator bellows systems employing either "gravity filling" or "gravity emptying" on disconnection.

The invention may be automatically turned on with the ventilator and is designed to require no setting of the alarm.

However, the set low pressure level 10 may be varied depending on the circumstances and, in particular the patient, being ventilated. In neonates this may be set as low as 4 or 5 cm. $H_2O$ and for adults may be set up to 8–9 cm. $H_2O$. Setting this low pressure datum may be done at the factory or, under the appropriate supervisory control, at the site of use and may involve a continuous control over a range, for example of from 4–9 cm. $H_2O$, or a simple upper/lower limit switch may be employed corresponding to respectively either adult or neonate use.

The method of the present invention would also have application to monitoring the disconnection of a patient under continuous positive airways pressure (CPAP), where such a mode is provided in a ventilator. CPAP is employed to aid gas exchange, for example in patients recently released from mechanical ventilation under intensive care and a delay of 20 seconds is generally employed before an alarm is activated. The present method would activate an immediate alarm, for example once the pressure fell to a set level. A delay of the type described above (0.1 seconds) may be employed to ensure the pressure switch is effectively closed before triggering the alarm, for example to compensate for switch bounce.

Figure 3:
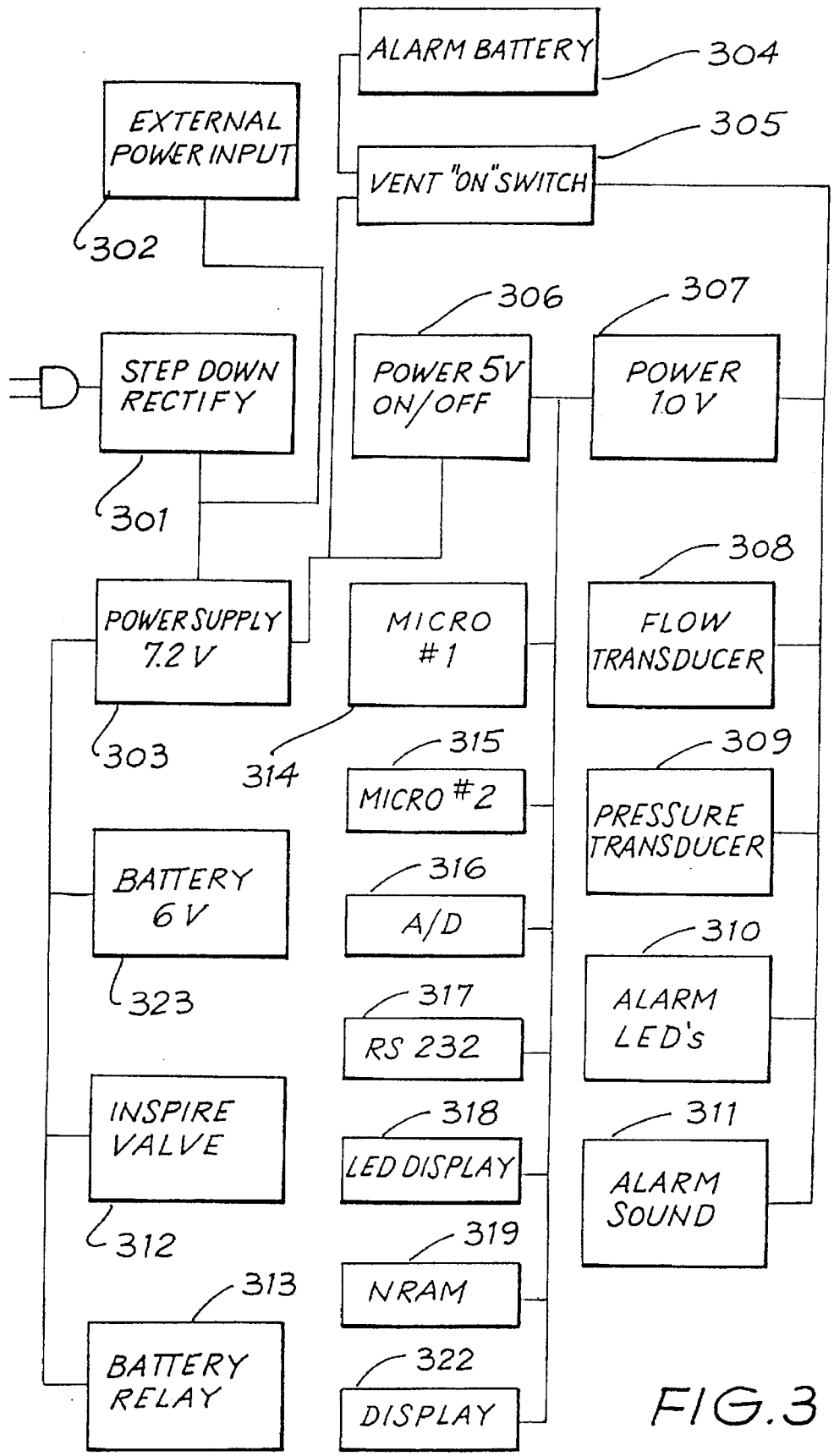
FIG. 3 shows a block diagram of a micro controller implementation according to a second embodiment of the invention.

The embodiment of FIG. 2 has been described with respect to an electromechanical implementation of the invention. A second embodiment will now be described with respect to FIGS. 3–5 and involves the use of a microprocessor, microcomputer or micro controller (these terms being considered synonymous for the purpose of this description) to analyse the pressure variations within a ventilation cycle and to provide the necessary indication under software control. In this embodiment, referring to FIG.3, the output of the pressure sensor 309, a normal feature of a ventilator of this type, may be of an electronic form which can be digitized by an analogue to digital converter 316 to be analysed by the micro controller 314 under software control.

The analogue to digital converter 316 may also be used to digitise the output from a patient flow transducer 308, the timing controls, which are adjustable and accessible from the control panel 318, and the battery monitor relay 313. The battery monitor relay 313 controls charging of a backup battery to be used in the case of mains failure. The flow transducer 308 provides a voltage at its output proportional to the pressure differential imposed across it from a flow detecting device (a pneumotach) which can be of any type well known in the art which provides a pressure differential proportional to the flow through it. The micro controller 314 also senses whether the inspiratory valve 312 is open or closed, which signals whether the ventilator is in an inspiratory or expiratory phase of its cycle.

Micro controller 314 may have an optional input/output communication interface 317, for example an RS232 serial port and may further have a second micro controller 315 controlling external devices such as printer 321, printer power supply 320 and graphic display 322 displaying the ventilator parameters.

The micro controller 314 controls the general operation of the ventilator including signalling an alarm condition indicative of a leak or a disconnection and the description below will be limited to illustrating the operation of the micro controller 314 with respect to the latter (ventilator disconnect alarm) feature only.

It is contemplated that the first step in the alarm indication is to turn a light emitting diode or diode(s) (LEDs) 310 alternatively on and off and after a subsequent delay to sound an audible alarm (if the condition has not been corrected) such as alarm sounder 311 as will be described below. Other forms of alarm indication may be employed within the knowledge of a person skilled in the art.

The micro controller 314 has a number of power supplies in order to ensure proper functioning of the ventilator. Primary power supply includes a transformer/rectifier 301, connected to the mains, supplying approximately 12 volts DC, or input may be supplied from an optional external power input 302. Power from supply 301, or 302 is connected to the voltage regulator circuits 303, 306 and 307 which in turn operate the electronics and other functions of the ventilator. Circuit 303 provides a switched mode power supply providing 7.2 volts limited to approximately 600 milliamps.. A battery may optionally be connected to regulated supply 303, for example a six volt acid gel battery 323 to continue to operate the ventilator in the event of failure of the mains or the optional input 302. The alarm circuitry has its own backup battery 304.

When power from 305 is present at the input to power supply 306, the latter provides a 5 volt power supply. Power supply 306 includes an on-off switch and feeds power supply 307 which provides a switched mode power supply of 10 volts.

Power supply 307 supplies the flow transducer 308, the pressure transducer 309, the alarm LEDs 310 and the alarm sounder 311 with power, and supplies power to regulated supply 306 in the absence of power from ventilator "on" switch 305. Switch 305 enables power from alarm battery 304, supply 303, and battery 323 to be connected to supply 306, the flow transducer 308, the pressure transducer 309, the alarm LEDs 310 and the alarm sounder 311.

Power supply 306 supplies the micro controllers 314,315 and other equipment connected to them such as the analogue to digital converter 316, the communication interface 317, the control panel display 318, the graphic display 322, the non volatile random access memory 319 with real time clock. Power supply 303 charges the standby battery 323 and operates the inspiratory valve 312 and the battery monitor relay 313.

Figure 4:
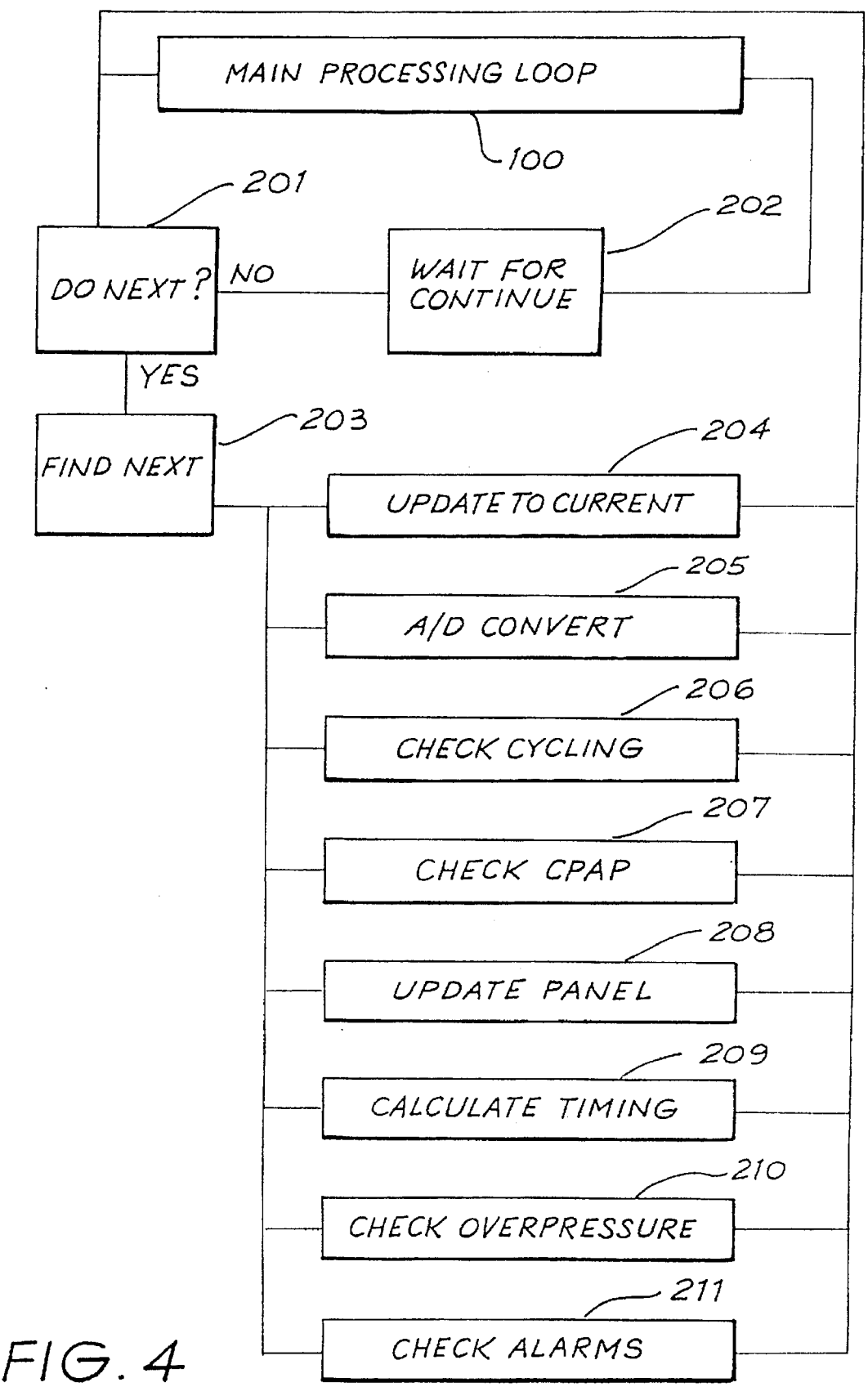
FIG. 4 shows in block diagram form the software sub routines contained within the main processing loop with reference to the embodiment of FIG. 3.
Figure 5:
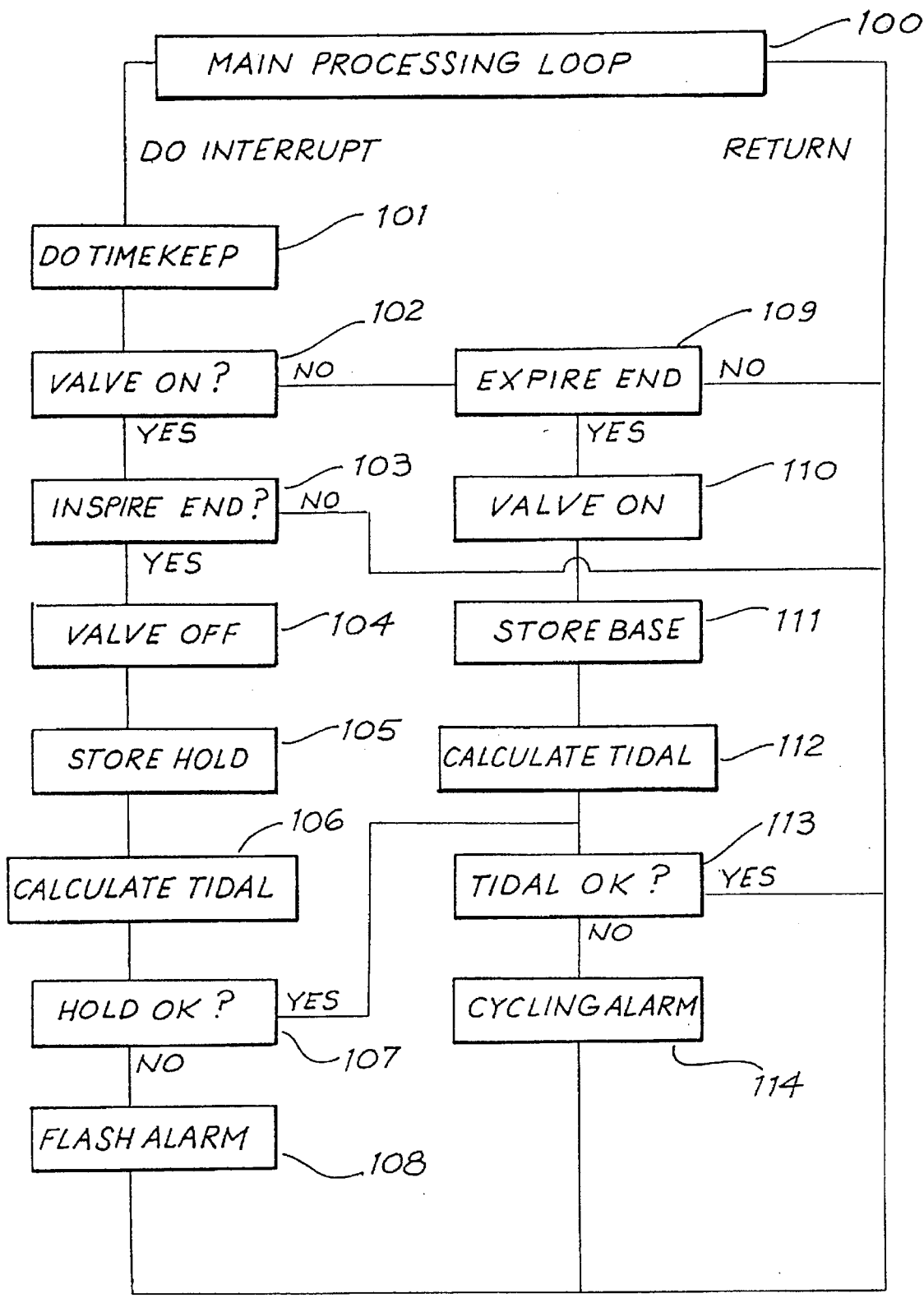
FIG. 5 shows the flow diagram for the interrupt routine employed in the embodiment of FIG. 3.

In FIGS. 4 and 5 the operation under software control of micro controller 314 is outlined in flow diagrams. The monitoring of the disconnect/leak functions are implemented in both the main processing loop, which is illustrated in FIG. 4, and the interrupt routine, which is illustrated in FIG. 5.

The interrupt routine follows a series of steps starting at step 101. When an interrupt occurs, an update Of the internal timers used to control the ventilation cycle and the alarm delay timing (step 101) is performed. Next the phase of the ventilation cycle is determined (step 102) by determining if the inspiratory valve is on and, if so, proceeds to determine if the inspiratory phase has been completed (step 103). If the inspiratory valve is not on then the sequence proceeds to determine if the expiratory phase has timed out (step 109). If either the inspiratory phase (step 103) or the expiratory phase (step 109) is not yet timed out then the programme returns to the start of the sequence at 100. If the inspiratory phase has timed out then steps 104–108 are performed whereas if the expiratory phase has timed out then steps 110–114 are performed.

Referring to steps 110–114, once the expiratory phase has timed out the inspiratory valve is turned on (step 110). The pressure at the start of the inspiratory phase, i.e. from gas remaining in the patient's lungs, is measured and its value stored, being labelled the patient base pressure (step 111). The maximum pressure achieved during the inspiratory phase is also sensed and stored as the patient hold pressure. This pressure is subtracted from the patient base pressure to determine a patient tidal pressure (step 112), that is the pressure difference between that at the beginning and the end of the inspiratory phase. This tidal pressure is then compared with a stored value therefor (step 113), and if the pressure difference is greater than the stored value, then the programme returns control to the main processing loop 100. If not, step 114 is performed which turns on a visual indicator, for example a LED indicating that the ventilator is not cycling and sets a flag to indicate this fact, subsequently returning control to the main processing loop 100.

If step 103 indicates that the inspiratory phase has timed out, then the programme steps 104–108 are performed. The inspiratory valve is turned off (step 104). The pressure from the patient at this stage is stored as a patient hold pressure (step 105). The patient base pressure for example as determined at step 111 is subtracted from this patient hold pressure and stored as the patient tidal pressure (step 106). The patient hold pressure is compared with a stored expected value for this parameter (step 107) and if the patient hold pressure is less than the stored value then an alarm state is indicated (step 108). If the patient hold pressure at this step is greater than the stored value then the programme compares the patient tidal pressure measured at step 106 with the patient tidal pressure measured at step 112 and again if the measured value is greater than the stored value terminates processing returning it back to the main processing loop 100. Otherwise, an alarm is indicated (step 114), as stated above, for example by flashing a light emitting diode on the display panel of the ventilator.

If an alarm was indicated at steps 107, 108 then in addition to an alarm indicator being activated then an alarm flag is set indicating that a disconnection has occurred. This can be used to time the activation of a subsequent audible alarm.

The main processing loop of FIG. 4 embodies a multitasking system which is synchronised to the interrupt routine shown in FIG. 5. It does this by calculating the time to the next interrupt and determining if another subroutine can be run (step 201). If there is not sufficient time then it waits to be synchronised by the interrupt routine (step 202). If there is enough time then it finds the next subroutine in the queue to be run (step 203) and then proceeds to execute the next such one of subroutines 204–211, a brief description of which follows.

Subroutine 204 updates a second, optional micro controller 315 when present. This micro controller 315 is used for:

(a) Graphically displaying ventilation parameters and alarm conditions by way of a number of display systems for example liquid crystal displays, vacuum fluorescent displays or light emitting diodes or other type of display as well known to a person skilled in the art;

(b) Printing out the ventilation parameters and alarm conditions to a printer;

(c) Storing calibrations and set up parameters on a non volatile random access memory; and (d) Determining the time and date from a real time clock contained in module 319.

Subroutine 205 controls the analogue to digital converter 316 which inputs to the micro controller 314 digitised signals from the patient pressure transducer 309, the (optional) patient flow transducer 308, the voltage of the main battery 323, the voltage of the alarm battery 304, and the set values for the tidal pressure alarm, the "not-cycling" alarm and ventilator cycle timing. The latter three parameters are indicated and settable by potentiometers mounted on and accessible from the control panel 318.

Subroutine 206 checks the ventilator cycling when the CPAP mode of ventilation is not invoked. It checks the patient pressure and if the patient pressure exceeded the datum 10 as shown in FIG. 1 (a) during the inspiratory cycle it causes the disconnect alarm flag to be set or, in other words, if the pressure drops below the patient hold alarm value before the end of the inspiratory cycle. If the patient pressure exceeds the datum 10 this subroutine 206 causes the not cycling alarm flag to be reset and the timing cycle for this alarm to be reset. If the CPAP mode of ventilation has been invoked then subroutine 206 returns to the main processing loop 100 to continue at step 201.

Subroutine 207 determines if the CPAP mode of ventilation has been invoked and then checks that the patient pressure is above a value set in software called the CPAP alarm set. If the patient pressure does not exceed this set value then the subroutine 207 sets the not cycling alarm flag. If the patient pressure does exceed the CPAP alarm set then the sub routine 207 resets the not cycling alarm flag.

Subroutine 208 updates the data which is displayed by the display light emitting diodes (LEDs) mounted on the control panel 318.

Subroutine 209 calculates the timing parameters for the expiratory and the inspiratory phase used by the interrupt routine described above with respect to FIG. 5.

Subroutine 210 checks for over pressure by comparing the patient pressure to a predetermined value stored in memory and called the over pressure alarm set. If the stored value is exceeded then subroutine 210 sets an over pressure alarm flag. Otherwise, if the patient pressure does not exceed the stored value then the over pressure alarm flag is reset.

Subroutine 211 checks the various alarm flags including the "not cycling" alarm flag, the over pressure alarm flag, the disconnection alarm flag and the low battery alarm flag and any other internal operating flags. If any of these flags are set for longer than their respective timings would allow then an audible alarm 311 and an appropriate alarm visual indication such as LED 310 are enabled as stated above.

The above subroutines and software control of the ventilator disconnect alarm function are to be seen as exemplary of the invention and not restricting in the interpretation thereof.

Testing for both disconnection and leaks was carried out on both adult and pediatric circuits. The adult circuit consisted of a circle system incorporating a soda-lime absorber. The dump valve was closed and the ventilator connected so as to replace the re-breathing bag. The pediatric system was a T piece with the ventilator connected to the expiratory limb. Tests were performed with a Campbell ventilator model Campbell/Ulco Mark 5 EL having a timed-cycle, and being volume limited as above referred to, with a bellows systems employing "gravity emptying" on disconnection.

The ventilator drive pressure was set at levels determined at infinite resistance, that is the pressure inside the bellows with the outlet completely obstructed. The ventilator flow settings were set corresponding to the ventilator acting as a pressure generator or alternatively as a flow generator. For leak testing the ventilator pressure generator setting was used throughout for testing both the adult and pediatric circuits. In all cases the disconnection was between the endotracheal connector and the endotracheal tube while for leak testing the leak site was adjacent to this.

The orifice sizes for the disconnections and leaks were obtained by using straight plastic endotracheal connectors. In testing for disconnections, the details were noted as to the smallest size of connector which registered the disconnection under a variety of ventilating parameters.

A test lung was used to record the tidal volumes for the various leak conditions. This was a Bio-Tek ventilator tester model VT2 which provided a printout of respiration rate, tidal volume, minute volume and inspiratory:expiratory (I:E) ratio. For adult testing, lung compliance was set at 20 ml. per cm. $H_2O$ and at 50 ml. per cm. $H_2O$. For pediatric testing, compliance was set at 3 ml. per cm. $H_2O$.

The adult airway resistance used in the test lung had a value of 8 cm. $H_2O$/liter/second and the pediatric airway resistance was 23 cm. $H_2O$/liter/second with both measured at 30 liters/min flow.

For adult circuit leak testing, the ventilator was set to a tidal volume of 500 ml. an inspiratory time of 1.5 seconds, an expiratory time of 3 seconds and a drive pressure of 40 cm. $H_2O$ with maximum entrainment.

For paediatric leak testing the ventilator was set to a tidal volume limit of 100 ml. an inspiratory time of 0.5 seconds, an expiratory time of 1.0 seconds, a ventilator drive pressure of 10 cm. $H_2O$ with maximum entrainment and the fresh gas flow was set at 3.0 liters per minute.

Under these conditions the sensitivity of the ventilator alarm was tested several times against a water manometer and consistently registered a threshold of 6.5 cm. $H_2O$ below which the alarm was activated.

Other embodiments are possible within the knowledge of a person skilled in the art.

What we claim is:

1. A method for supervising the operation of a ventilating apparatus having a ventilation cycle and for indicating a failure to adequately ventilate an intubated patient, comprising:
   a) measuring a pressure of a gas supplied to a patient over each ventilation cycle, each said ventilation cycle including an inspiration phase, and each said inspiration phase having an identical set period of time (T) less than the length of said inspiration phase; and
   b) immediately activating an alarm if during said set period of time (T) said pressure falls below a threshold, said threshold being in the range of 4–9 cm $H_2O$.

2. The method for supervising the operation of a ventilating apparatus and for indicating a failure to adequately ventilate an intubated patient according to claim 1, wherein:
   said set period of time (T) is substantially similar to, but less than, said inspiration phase.

3. An apparatus for indicating abnormal ventilation of a patient for use with a ventilator having a ventilation cycle, comprising:
   a) sensing means for sensing a pressure of a gas supplied to a patient during said ventilation cycle, said ventilation cycle including an inspiration phase, and said inspiration phase having a set period of time (T) less than the length of said inspiration phase;
   b) setting means for setting said set period of time (T) during said inspiration phase; and
   c) indicator means sensitive to said set period of time (T) and to said pressure for immediately indicating an abnormal operation of the ventilator when said pressure falls below a threshold during said set period of time (T), said threshold being in the range of 4–9 cm $H_2O$.

4. An apparatus for indicating abnormal ventilation of a patient according to claim 3, wherein:
   said indicator means includes a first pressure switch and a second pressure switch, said first pressure switch being closed when said pressure is below said threshold and said second pressure switch being closed throughout said set period of time (T), and
   wherein said abnormal ventilation being indicated when both said first pressure switch and said second pressure switch are closed.

5. An apparatus for indicating abnormal ventilation of a patient according to claim 4, wherein:
   said set period of time (T) is substantially similar to, but less than, said inspiration phase.

6. The apparatus for indicating abnormal ventilation of a patient according to claim 3, wherein:
   said set period of time (T) is substantially similar to, but less than, said inspiration phase.

* * * * *